(12) United States Patent
Emmert et al.

(10) Patent No.: US 8,969,093 B1
(45) Date of Patent: Mar. 3, 2015

(54) CALIBRATION METHOD AND DEVICE FOR REMOTE LOCATION TESTING INSTRUMENTS

(71) Applicants: Gary Lynn Emmert, Collierville, TN (US); Paul S. Simone, Jr., Cordova, TN (US)

(72) Inventors: Gary Lynn Emmert, Collierville, TN (US); Paul S. Simone, Jr., Cordova, TN (US)

(73) Assignee: University of Memphis Research Foundation, Memphis, TN (US)

( * ) Notice: Subject to any disclaimer, the term of this patent is extended or adjusted under 35 U.S.C. 154(b) by 134 days.

(21) Appl. No.: 13/836,125

(22) Filed: Mar. 15, 2013

(51) Int. Cl.
*G01N 1/00* (2006.01)
*G01N 33/18* (2006.01)
*G01N 30/38* (2006.01)

(52) U.S. Cl.
CPC .................................... *G01N 33/18* (2013.01)
USPC ......... 436/125; 436/124; 73/61.55; 73/64.56; 250/304

(58) Field of Classification Search
USPC ........ 436/124, 125; 73/61.55, 64.56; 250/304
See application file for complete search history.

(56) References Cited

U.S. PATENT DOCUMENTS 7,987,701 B2 * 8/2011 Emmert et al. ............... 73/61.56
8,336,371 B2 * 12/2012 Emmert et al. ............... 73/61.55

OTHER PUBLICATIONS

Geme, G. et al. Measuring the concentration of drinking water disinfection by-products using capillary membrane sampling—flow injection analysis.(2005). Water Research. 39: 3827-3836.*

* cited by examiner

*Primary Examiner* — Rebecca M Fritchman
(74) *Attorney, Agent, or Firm* — William S. Parks; Wyatt, Tarrant & Combs, LLP

(57) ABSTRACT

Constant calibration methods and apparatuses for analytical devices that are located in remote positions in order to allow for reliable and automated measurements of various contaminants within water or other liquid samples. The proposed calibration systems allow for certain methods to measure total amounts of certain trihalomethane and haloacetic acid contaminants, at least, in drinking water samples from such remote locations, through the utilization of a standard addition introduction of known concentrations of such contaminant compounds within target samples, followed by separation through a capillary membrane sampling device and measurement of such different contaminants via flow injection analysis (FIA). In such a manner, the on-line, remote system provides the necessary reliability for a water utility or like entity on which to base any further needed water treatment activities without having to perform such measurements in a distinct lab setting.

1 Claim, 3 Drawing Sheets

CALIBRATION METHOD AND DEVICE FOR REMOTE LOCATION TESTING INSTRUMENTS

FIELD OF THE INVENTION

The present invention relates to constant calibration methods and apparatuses for analytical devices that are located in remote positions in order to allow for reliable and automated measurements of various contaminants within water or other liquid samples. The proposed calibration systems allow for certain methods to measure total amounts of certain trihalomethane and haloacetic acid contaminants, at least, in drinking water samples from such remote locations, through the utilization of a standard addition introduction of known concentrations of such contaminant compounds within target samples, followed by separation through a capillary membrane sampling device and measurement of such different contaminants via flow injection analysis (FIA). The novel remote calibration method injects such known concentrations via a syringe at regular intervals in a manner to provide a baseline measurement that accords a reliable comparison with the unknown amounts present within the drinking water samples at issue. In such a manner, the on-line, remote system provides the necessary reliability for a water utility or like entity on which to base any further needed water treatment activities without having to perform such measurements in a distinct lab setting.

BACKGROUND OF THE INVENTION

Drinking water has been, and continues to be, heavily treated for bacteria and other microscopic organisms that may cause infection in humans and other animals subsequent to consumption. In order to disinfect water supplies, halogenated materials have been introduced therein that have proven more than adequate for such a purpose. Unfortunately, although such halogenated compounds (chlorinated and chloraminated types, primarily) exhibit excellent disinfection capabilities, when present within aqueous environments at certain pH levels these halogenated compounds may generate byproducts that may themselves create health concerns. The United States Environmental Protection Agency (USEPA) in fact regulates five specific types of haloacetic acids within drinking water, monochloroacetic acid, dichloroacetic acid, trichloroacetic acid, monobromoacetic acid, and dibromoacetic acid, as well as four types of trihalomethanes, chloroform, bromodichloromethane, dibromochloromethane, and bromoform. Removal of such compounds from drinking water is not possible as for typical chlorinated and brominated disinfecting compounds, at least not at the same reliability level as for the disinfecting agents. Thus, residual amounts may remain within treated water supplies that may require further removal processes to be undertaken. Of course, if the level of contamination is sufficiently low, initiation of such potentially expensive removal steps would be unwise from an economic perspective.

The USEPA currently has set a maximum contaminant level for the five haloacetic acids (collectively referred to as HAA5; four other haloacetic acids are currently not regulated by the USEPA, bromochloroacetic acid, bromodichloroacetic acid, dibromochloroacetic acid, and tribromoacetic acid; including these, the total haloacetic acid group is known as HAA9) at a total amount of 0.060 mg/L and for the trihalomethanes at 0.080 mg/L. It is thus important to reliably analyze and measure the total amount of such contaminants in order to determine if removal if necessary.

The USEPA has instituted its own testing methods for such a purpose. One, known as EPA 552.2, involves the liquid-liquid extraction of haloacetic acids from water sources into methyl-t-butyl ether, followed by derivatization with acidic methanol to form the corresponding haloacetic acid methyl esters. Analysis by gas chromatography-electron capture detection provides reliable measurements of the haloacetic acid amounts present within the subject water supply. The other, USEPA 552.3, is a derivative of the first with optimizations of acidic methanol neutralization procedures for improvement in brominated trihalogenated haloacetic acid species. These general processes have been found to have numerous drawbacks, however. For instance, injection port temperature can affect debromination of certain haloacetic acid species (particularly tribrominated types) that may lead to under-representation of the amount of such contaminants present within the tested water source. Likewise the water content of the methyl-t-butyl ether extract may decarboxylate the haloacetic acids, again leading to an under-reporting of the actual amounts present within the test sample. Furthermore, the involved processing needed to actually undergo such analysis makes an on-line protocol rather difficult to implement, particularly when hourly sampling is necessary. Other derivatization methods have been either followed or suggested for gas chromatography analyses of drinking water sources as well, including utilizing diazomethane, acidic ethanol, and aniline. Such reactant-based measurements, however, all suffer the same time and labor-intensive problems as with the two EPA test procedures noted above. As such, on-line analysis through these protocols are difficult, expensive, and labor intensive to implement.

The most common USEPA testing protocols for THMs include USEPA method 502.2 and 524.2. Both methods use purge and trap technology to volatilize the THMs from a drinking water sample onto an adsorbent trap that concentrates the THMs. The adsorbent trap is then rapidly heated to desorb the THMs onto the gas chromatography column for separation. USEPA 502.2 uses an electrolytic conductivity detector to determine THM concentrations and USEPA 524.2 uses a mass spectrometer. Both of these methods provide reliable measurements of THMs concentrations in drinking water. However, both methods are expensive and neither method can be considered portable.

Measurement at the source (i.e., within a water purification plant location) may be effective for system-wide average readings; however, in the large supplies of water at such locations, the chances of proper sampling to that effect may be suspect since the contaminants may be present in varied locations, rather than definitely mixed throughout the tested water supply itself. Additionally, testing may not uncover the actual level of residual haloacetic acid or trihalomethane disinfection byproducts prior to the water supply being disbursed to distant dispense sites (transfer pipes, homes, schools, businesses, etc.). In any event, there is a relatively new rule in place that requires utilities to provide evidence of compliance with haloacetic acid levels at multiple locations, rather than a straightforward system-wide average. Thus, since the above-described derivatization procedures with gas chromatography-electron capture detection analytical methods and purge and trap gas chromatography with either previously mentioned detector are not suitable for a uniform haloacetic acid or trihalomethane measurement scheme. There is thus a drive to implement remote testing via real-time, on-line methods for water supply HAA5, and, more importantly, for HAA9 contaminant level measurements, not to mention for the four trihalomethanes, too.

Such a desirable on-line procedure has been difficult to achieve, however, particularly as it pertains to the determination of not only the amount of haloacetic acid and/or trihalomethane species, but also the amount of each species present within the tested water source. High performance liquid chromatography, utilizing electrospray ionization-mass spectrometry or ultraviolet absorbance as the detector, has been attempted, as well as ion chromatography, with membrane-suppressed conductivity detection or, as well, ultraviolet absorbance detection. Other attempts with inductively coupled plasma-mass spectrometry and electrospray ionization-mass spectrometry coupled with ion chromatography have been followed as well for this same purpose. The detection level can be as low as 0.5 to less than 10 µg/L for HAA9 species, but only subsequent to sample preparations. The sensitivity and selectivity of ion chromatography and high performance liquid chromatography methods are easily sacrificed without the cumbersome preparations in place, therefore requiring operator intervention during analysis. Again, this issue leads to serious drawbacks when on-line implementation is attempted as well.

Another methodology that has proven effective to a degree is post-column reaction-ion chromatography. This has shown promise, but only in terms of quantifying bromate ion concentrations in drinking water samples at a single microgram per liter level. This dual selectivity form (separation by ion chromatography column as well as the selective reaction with the post-column reagent with the analyte) offers an advantageous test method over the others noted above, except for the presence of more common anions, specifically chloride, at much higher concentrations within the sampled drinking water supply (mg/L instead of µg/L). It was then undertaken to combine the separation capabilities of ion chromatography with the reaction of the haloacetic acid species with nicotinamide, followed by fluorescence detection to measure the individual and total HAA5 concentrations in drinking water at the single µg/L level. The problem with such a protocol, unfortunately, was that bromochloroacetic acid interfered with dichloro- and dibromo-acetic acid quantifications. Despite this problematic limitation, it was determined that fluorescence detection provided a much improved detection protocol in comparison with ultraviolet absorbance and mass spectrometry possibilities. Thus, although such a fluorescence method of detection, coupled with the post-column reaction (again with nicotinamide reagent) and ion chromatography, exhibited the best results in terms of an on-line test method for HAA5 drinking water contaminant measurement levels, there remained a definite need for improvements in total haloacetic acid measurements and identifications within such test samples. Gas chromatography-based analysis is typically used for THMs combined with multiple sample preparation techniques and different detectors. USEPA 502.2 and 524.2 have previously been discussed, but suffer from being expensive and not portable. Capillary membrane sampling-gas chromatography with electron capture detection has been previously used to monitor THMs on-line as well as the on-line, purge and trap-gas chromatograpy with dry electrolytic conductivity detection. The capillary membrane sampling—gas chromatography with electron capture detection uses a membrane device to pervaporate the THMs across a silicone rubber membrane into a stream of nitrogen, which is then separated by a gas chromatography and detected with electron capture detection. The on-line purge and trap—gas chromatography instrument uses a silicone rubber membrane in similar fashion as the capillary membrane sampling device, but the THMs are swept onto an adsorbent trap for concentration. The THMs are then desorbed, separated on a GC column and detected with a dry electrolytic conductivity detector. To date, however, there has not been an analytical test protocol that has permitted implementation of such a systems within an on-line real-time monitoring procedure with an acceptable degree of reliability.

Of even greater interest, however, is the capability of any such system to provide reliable testing results at effective time intervals. Past measuring techniques have proven effective on monthly or quarterly schedules; desired timeframes, however, are hourly, instead. The past analytical procedures, noted above, are rather difficult to employ at remote locations to begin with; to attempt testing every hour further exacerbates an already cumbersome procedure. On-line monitoring, though highly prized in the drinking water industry, has thus proven difficult to employ. Even with mobile methods in use, bench-top scale instruments have been necessary, rather than portable devices for such applications. Additionally, the reliability of any such on-line monitoring system has been highly suspect due to fluctuations in readings as calibration for short-term measuring intervals has not been easily incorporated therein, let alone actually followed.

Additionally, and to compound the difficulties associates with on-line monitoring systems of this type, the reliability of measurement and analysis of water samples is based upon the capability of the overall system to provide reproducible results at different times. With a standard sample provided for rather long periods of time until a new sample may be introduced within the remote system, the possibility that the standard has been altered through temperature fluctuations over time, or growth or production of undesirable organisms or chemical species therein during storage may cause problems ultimately in the resultant measurements. There thus exists a need to provide an effective remote calibration system in order to alleviate such potential analytical disparities. To date, there exists no reliable on-line continuous monitoring system for the type and amount of drinking water disinfection byproducts utilizing a calibration procedure at a remote location. Such a continuous system would basically involve testing procedures that are automatically undertaken remotely in regular intervals, whether by the hour, minute, day, etc. The ability to undertake remote testing and analysis permits on-line and real-time quantification and/or qualification of potential contaminants (i.e., total trihalomethane and haloacetic acid species) with little human involvement in the overall testing procedures thus provides significant efficiencies to such overall water sample testing capabilities. In order to provide reliable data in such remote locations, there is an expressed need to provide such effective calibration of the overall testing system in order to ensure the instrumentation is properly measuring specific levels, particularly at rather low concentrations. The capability of not only providing an on-line method for such contaminant analysis, but, as well, an overall calibrated system that functions remotely, too, would thus permit the greatest level of reliability possible on which a water utility or other like entity would base its water treatment activities, particularly when based upon water samples located within transfer lines, and not solely present in a laboratory. To date, although certain calibration methods have been accorded laboratory settings for certain liquid sample analytical processes, the ability to provide remote calibration protocols that render highly reliable measurements without human interaction or like involvement has not been provided the pertinent industries.

ADVANTAGES AND SUMMARY OF THE INVENTION

It is an advantage of the present invention to provide a reliable on-line drinking water analytical protocol for determining total trihalomethane and total haloacetic acid concentrations in drinking water. It is an additional advantage of the invention to provide reliable data at any location along a drinking water supply line without need for operator involvement by implementing automatic operation and calibration of said invention. Yet another advantage is the ability to deliver a calibration standard to compensate for projected levels of trihalomethane species that do not traverse a separation membrane, thereby permitting generation of sufficiently reliable data for an operator to determine if further actions are necessary to correct for high levels of halogenated contaminants in the tested water supply.

Accordingly, the invention encompasses a method of analyzing drinking water samples in an on-line procedure and at a remote location along a drinking water supply line, said method comprising:

a) providing at least one initial stream of drinking water that has been disinfected with chlorinated or chloraminated disinfectants within a first tube;

b) separating said stream into at least two different subsequent streams, wherein i) a first separated stream is transferred directly into a second tube, and ii) a second separated stream is transferred into a third tube wherein it is injected remotely with a standard calibration water sample, wherein said standard water sample includes a predetermined concentration of trihalomethanes and haloacetic acids therein;

c) providing a first separate stream of reagent water, wherein said reagent stream is present within a fourth tube into which said second tube including said first stream of drinking water is introduced to form a first capillary membrane sampling device;

d) providing a second separate stream of reagent water, wherein said reagent stream is present within a fifth tube into which said third tube including said second stream of drinking water and said standard water sample is introduced to form a second capillary membrane sampling device;

e) transporting said first separated stream of drinking water through said first capillary membrane sampling device, such that the majority of all volatile trihalomethanes present within said first separated drinking water stream traverse the membrane of said second tube into said stream of reagent water within said fourth tube to form a first trihalomethane-containing stream, and wherein any haloacetic acids present within said first separated drinking water stream will remain therein and within said second tube to form a first haloacetic acid-containing stream;

f) transporting said second separated stream of drinking water through said second capillary membrane sampling device, such that the majority of all volatile trihalomethanes present within said second separated drinking water stream traverse the membrane of said third tube into said stream of reagent water within said fifth tube to form a second trihalomethane-containing stream, and wherein any haloacetic acids present within said second separated drinking water stream will remain therein and within said third tube to form a second haloacetic acid-containing stream;

g) transporting the first trihalomethane-containing stream and the first haloacetic acid-containing stream to a first multi-port injection valve, wherein said valve is configured to inject either said first trihalomethane-containing stream or said first haloacetic acid-containing stream to a first mixing manifold at one time;

h) mixing either of said from step "g" streams with base and subsequently a fluorescing compound within said first mixing manifold to form a first fluorescing trihalomethane-containing stream or a first fluorescing haloacetic acid-containing stream therein;

i) transporting said fluorescing stream to a fluorescence detector to determine the concentration of either total trihalomethanes or total haloacetic acids within each stream through fluorescence detection; wherein only one of said fluorescing trihalomethane or said fluorescing haloacetic acid streams will be analyzed at any one time, while the other is passed through a return or waste line until said first multi-port injection valve is activated to send the other fluorescing stream to the be analyzed and the previously analyzed stream to a return or waste line;

j) simultaneously transporting the second trihalomethane-containing stream and the second haloacetic acid-containing stream to a second multi-port injection valve, wherein said valve is configured to inject either said second trihalomethane-containing stream or said second haloacetic acid-containing stream to a second mixing manifold at one time;

k) mixing either of said from step "j" streams with base and subsequently a fluorescing compound within said second mixing manifold to form either a second fluorescing trihalomethane-containing stream or a second fluorescing haloacetic acid-containing stream therein;

l) transporting said second fluorescing stream to a fluorescence detector to determine the concentration of either total trihalomethanes or total haloacetic acids within each stream through fluorescence detection; wherein only one of said second fluorescing trihalomethane or said second fluorescing haloacetic acid streams will be analyzed at any one time, while the other is passed through a return or waste line until said second multi-port injection valve is activated to send the other fluorescing stream to the be analyzed and the previously analyzed stream to a return or waste line;

and m) calculating total haloacetic acid and trihalomethane compound concentrations of all of said first and second fluorescing trihalomethane-containing and haloacetic acid-containing streams based on the fluorescence levels thereof in relation to a calibration point based upon the standard addition amount of trihalomethanes and haloacetics acids introduced in step b)ii);

wherein steps a) through l) are then repeated in intervals of between 10 and 120 minutes.

The calibration standard may be of any amount of the HAA9 or THM4 compounds, as long as a standard amount is introduced during each sample analysis and calibration step (and thus for each analytical test procedure). The injection is typically made through a syringe including a deionized water sample with set concentrations of the standard compound(s). The syringe is attached to means to activate movement thereof in order to provide direct injection of the standard sample within the drinking sample stream. In practice, though, any means to introduce a calibration sample may be utilized (including a vacuum pump, pressurized line with a proper valve device to allow and prevent liquid movement, peristaltic pump and the like) to effectuate the needed standard addition sampling. The resultant measurements are then provided in graphical form with a single reading for all THM compounds and the same for all HAAs. The user, either a human operator or, more likely, a computer-driven program, monitors the amounts under the curves for each class of compounds to determine if a baseline amount has been exceeded. In relation to the calibration standard, then, depending on which standard is added, the curve of the pertinent class of compounds will exhibit an increase that can then be factored out of the overall measurement, thereby providing a means to proportion the measured amounts to the standard. This method thus provides a greater reliability and, more importantly, potentially, more concise numerical value to the overall amount of HAA9 and THM4 present within the drinking water sample as a result.

Generally, then, a two-point standard addition (or "spike") protocol has been found herein to be surprisingly effective to provide the necessary and reliable curve for such an overall analytical on-line and remote method. The spike method involves the analysis of an unknown concentration sample against the analysis of an unknown sample to which is added a known concentration of a similar compound (the "spike"). In such an instance, the concentration of the unknown in the original sample can be calculated from the equation:

$$[X]_i = \frac{[S]_f}{(I_{s+x}/I_x) - (V_0/V)}$$

Where:
$I_{s+x}$=Signal of the spiked sample
$I_x$=Signal of the original sample
$[S]_f$=Spike final concentration
$V_0/V$=Dilution factor With a single THM and a single HAA (chloroform and trichloroacetic acid, for instance) used as the spikes for such measurements, the resultant drinking water samples can be analyzed with a certain degree of reliability as to the actual concentration of disinfectant by-products present within the tested samples through the utilization of the on-line FIA method. Such a "two point" standard addition technique better balances the quality of the desired result with the time available to carry out the technique under on-line conditions and time constraints. In other words, the introduction of the standard addition samples through remote means (syringe, peristaltic pump, piston pump, pressurized flow, etc.) imparts a more reliable end result measurement than without any spike (or calibration curve generation possibility) because of the unknown quality of the reagent water stream over time, as well as the potential inconsistencies of the amounts of halogenated species that are passing through the drinking water stream at any time. The lack of specific starting points in terms of proper fluorescence measurements thus could compromise the overall measured results and provide skewed data to the operator. With the standard addition calibration potential, however, the capability of factoring in standard concentrations of THM and HAA species, and thus the capability of removing from the resultant measured fluorescence curves the known quantities involved, the user can then easily determine the actual contaminant levels present within the drinking water streams at any point in time. The capability of performing such a reliable measured result through a totally remote process is highly unexpected, considering the difficulties in delivering reliable concentrations and samples in such a manner (without human operation) for an appreciable period of time. As such, the current invention does, in fact, permit quantification of both total trihalomethane and total haloacetic acid species within a subject drinking water sample to an extremely reliable degree, thus allowing a remote user to determine the potential harmful levels of such suspect carcinogenic compounds therein. Corrective measures may then be undertaken to resolve any potential harmful levels of halogenated contaminants within the subject drinking water line. The remote method and the entire instrument may be operated at any selected location along a drinking water supply line for such a purpose, as well.

The underlying analytical method itself encompasses, as noted above, a drinking water analytical instrument comprising of a capillary membrane sampling device attached to a ten-port valve which is attached to a mixing manifold which is attached to a fluorescence detector. The ten-port valve permits alternating injections of different streams of drinking water subsequent to separation of volatile trihalomethane compounds from the drinking water stream within the capillary membrane sampling device. The haloacetic acid compounds, being ionic in nature, do not cross the CMS barrier, thus remaining within the drinking water stream substantially in total. In actuality, the THM compounds do not completely pass through the membrane as at least some such compounds will not fully volatilize so as to be in proper form to transport in such a manner. It has been noted that anywhere from about 1 to 49% of such THM compounds may not pass through the membrane (more specifically within a range of from about 15-35%, more specifically about 25-30%), thus leaving a residual amount within the drinking water stream as well. Upon reaction with the fluorescing compound, prior to detection, a certain amount of THMs will also pass through the detector associated with the HAAs. In this situation, however, the resultant curves can be properly modified to take this into account (i.e., the HAA curve can be reduced another 25-30% to as measured and that amount can be transferred to the THM measurements), if necessary. As the overall amounts of such halogenated species are rather low initially, the amounts attributed to THMs under the HAA curves may actually be considered negligible under some conditions. In any event, such a remote on-line measurement protocol may account for any discrepancies in that manner, again, if necessary. All in all, the fact that such a potential result may occur at all lends credibility to the unexpected effectiveness of the overall inventive method permitting quantification of both total trihalomethane and total haloacetic acid species within a subject drinking water sample.

Such methods have permitted implementation of remote automatic testing procedures and instrumentation along any location of a drinking water supply line. As noted above, the previous analytical approaches suffered from necessary operator involvement, deleterious effects from reactants or simultaneously formed byproducts thwarting reliable measurements from being taken to ensure compliance with federal regulations. This present method and entire analytical instrument has overcome such limitations through the inclusion of an additional ten-port valve and on-line addition of a THM and HAA standard after separation of volatile trihalomethanes from haloacetic acids via CMS and with further refinement of a fluorescing step, all coupled with a remote detection process. The instrumentation does not require human operator involvement unless a breakdown or energy source failure occurs; for testing purpose, however, the analyses can be performed at regular intervals through computer processor control.

The separation of trihalomethanes from the drinking water stream(s) may be performed by a capillary membrane sampling device. In this manner, the drinking water stream is introduced within the device and the volatile trihalomethane compounds permeate across thin silicone membrane tubing and out of the drinking water stream itself for separation therefrom into an acceptor reagent water stream stream. In this manner, it is possible for the trihalomethanes to be separated from other contaminants within the drinking water stream that may compromise quantifications of such compounds subsequently due to reactions between such THM4 compounds and such other potential contaminants, among other reasons. The acceptor stream (such as reagent water) may be employed within the capillary membrane device to promote diffusion of the volatile THM4 compounds from the drinking water stream within the device itself.

Additionally, however, the inventive testing protocol potentially suffers from the lack of human involvement during such a remote location procedure due to the lack of continued long-term reliability of the testing materials themselves, particularly as it concerns the deterioration or impurity of standard water samples over time. As it should be well understood, standard water samples at remote locations may be susceptible to reactions with ionic species present therein that may impact the overall reliability of the tests over time. For instance, since a comparative water standard is necessary within the configuration noted above, the lack of human oversight and involvement requires the injection of a standard water sample during each regular test procedure. Should the standard water sample not be replenished with "fresh" sources over a certain period of time, the comparative water standard for the actual water samples to be tested against may skew the overall results such that the water system (and its operators thereof) may mistakenly accept a measurement as being within specifications that is, in actuality, well outside the range of HAA and/or THM levels. As such, as alluded to above, there remains a need to ensure reliable measurement protocols are in place for such remote testing procedures. The inventive calibration method certainly aids in this respect.

To that end, the replenishment of the calibration standard should be undertaken within a certain amount of time. Clearly, though, to provide hourly calibrations in a remote, on-line system would require a personal presence that defeats the purpose of such an overall analytical device. As it is, it has been found that intervals of 24 to 48 hours (up to possibly 72 hours) are sufficient for such a procedure, particularly in relation to the system developed herein. Thus, in order to provide a reliable calibration source, a new sample of predetermined spike concentrations needs to be provided within such time intervals. The capability of providing a reliable overall measurement of drinking water samples through such a calibration procedure that does not require on-site or spike sample replenishment every hour (or few hours) thus allows for the highly prized remote and on-line system to function properly.

The inventive calibration technique in thus an on-line procedure has never been provided previously. At remote locations, there are certain limitations in terms of reliability of standardized samples, at least, that have led, at least, to noticeable deficiencies in the reliability of such a protocol. As operators cannot be present for each and every hourly measurement, the institution of a calibration method overcomes the lack of operator presence and boosts reliability. Again, however, such a calibration step is not a simple step to initiate, ostensibly due to the remote location necessary for such an on-line monitoring system to be effective. The calibration technique required initial separation of the standardized test sample(s) from any drinking water test samples. Furthermore, the calibration protocol required, as well, the ability to introduce the standardized test sample(s) into typical water streams for proper measurements to be made in standardized (calibrated) fashion. Additionally, the injection valve configurations needed to permit reliable flushing of the test streams themselves in order to ensure contamination of the drinking water samples necessitating analysis would not occur. Lastly, as noted above, the standardized test sample(s) needed to be stored for extended periods of time without losing (or gaining) any pre-produced concentrations levels of trihalomethane and/or haloacetic acid; if the standardized samples did not remain as close to their pre-produced concentrations, the calibration would be skewed, thereby calling into question the overall veracity of the overall on-line monitoring system itself. Such single-point calibration (including standard addition) allows for sample concentrations to be calculated based off of a standard analyzed in the same run, thus compensating for any possible drift of the analyzer over the course of a long-term monitoring study. The typical approach is to run a 5-point calibration curve and three check standards. The analyzer is calibrated and the check standards ensure the analyzer is operating properly. However, external calibration has a chance to drift out of calibration due to a variety of factors including, reagent composition, lamp intensity drift, and pump tubing wear, whereas the single-point calibration technique and system component of the invention compensates for any potential drift during every analysis.

Beyond these novel on-line and remote calibration techniques, in order to attain the necessary levels of reliability for the actual test protocols themselves, the measurements of the trihalomethane and haloacetic acid amounts had to be comparable to those provided through the aforementioned USEPA 500 (including USEPA 552.3 and 524.2) series test protocols. As well, the ability to permit identification of the disinfectant byproduct compounds within the target drinking water sample must be at such a level that proper discernment of each class of compounds (Total THMs and Total HAAs) is necessary as well. Such has been attained with this inventive method.

DETAILED DESCRIPTION OF THE DRAWINGS AND PREFERRED EMBODIMENTS OF THE INVENTION

Figure 1:
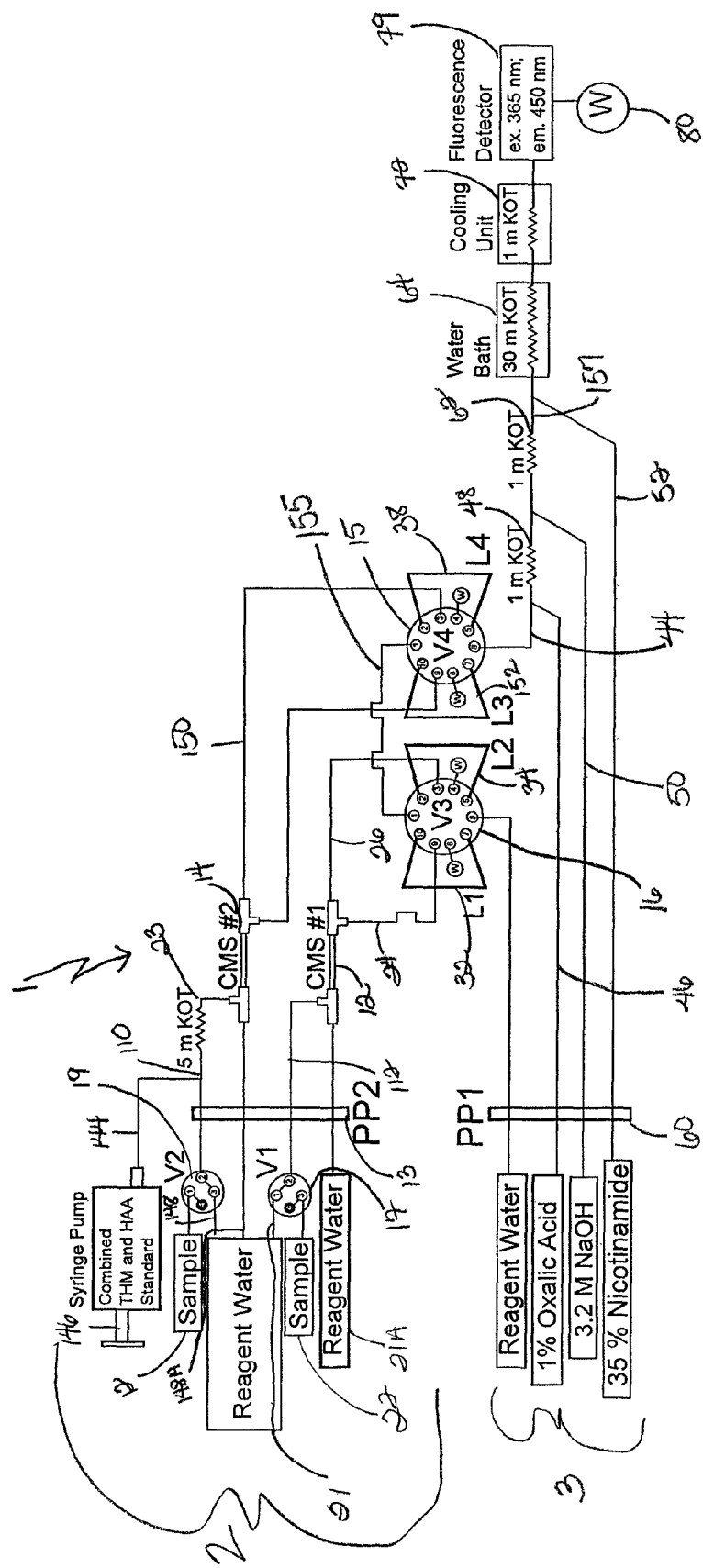
FIG. 1 depicts a broad schematic of the CMS-FIA analyzer for the on-line analysis of total trihalomethanes and total haloacetic acid concentrations in drinking water with a four-port injection valve in its 1 position and a ten-port injection in position 1 as well as a injected single point standard addition calibration component.
Figure 2:
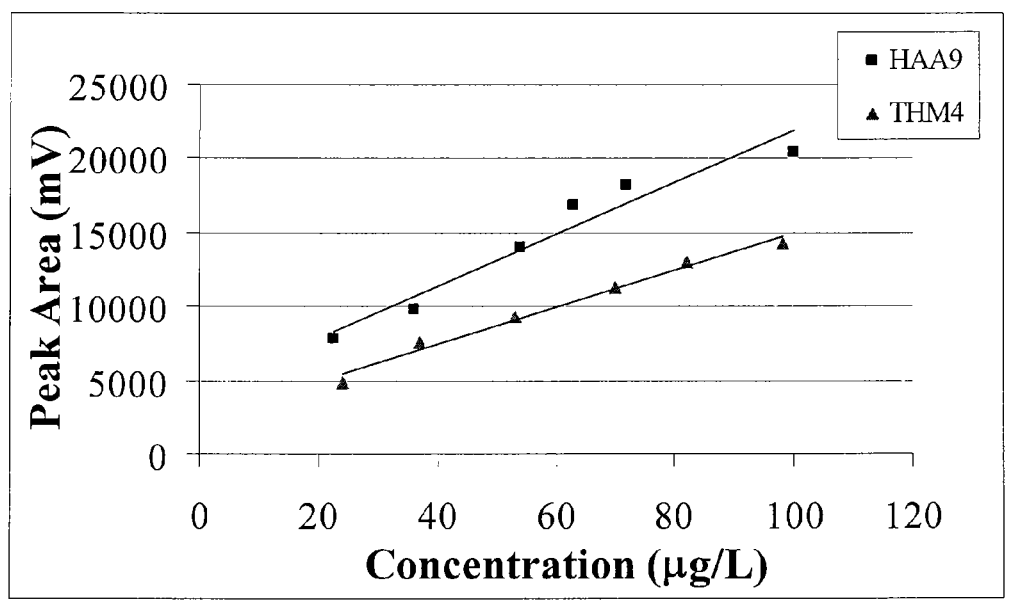
FIG. 2 is a graphical representation of external calibration plots of HAA9 and THM4.
Figure 3:
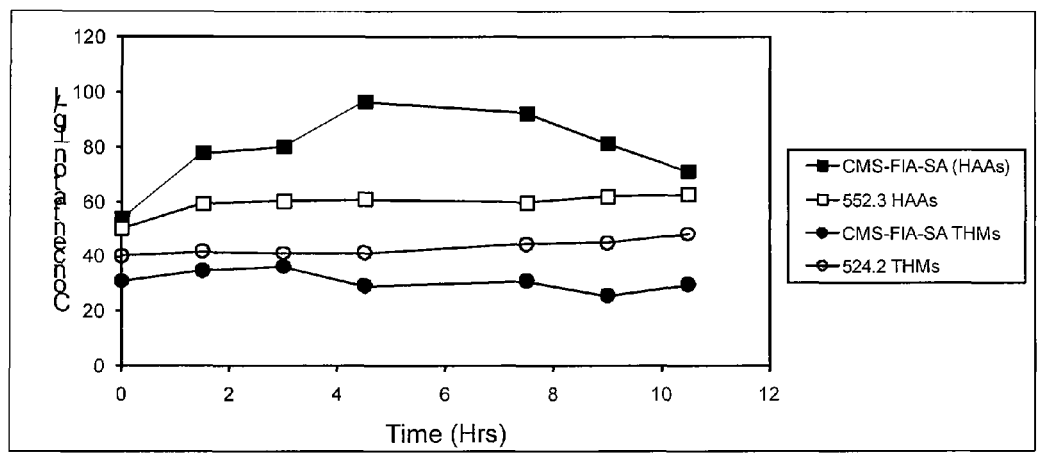
FIG. 3 is a graphical representation of the Concentration vs. time for Total THMs using CMS-FIA-SA and USEPA Method 524.2 and for Total HAAs using CMS-FIA-SA and USEPA Method 552.3.

There are two semi-independent systems on the single point standard—capillary membrane sampling—flow injection analyzer 1 (SPS-CMS-FIA): the sampling system 2 and the flow injection system 3 (FIG. 1). The sampling system 3 delivers THM or HAA samples 12 and the single point standard addition TCAA or chloroform standards 144 to the flow injection system 2. The sampling system 3 is comprised of a 4-channel peristaltic pump 13 (PP 2); two 4-port switching valves 17, 19 (V1, V2) (or any valve that provides reliable stream switching); a syringe pump 146 cooled to 4° C. (or any device which provides acceptable addition of the standard to a flowing stream of water); a 4 m knitted open tubular reaction coil (KOT) 23 (or any device that provides sufficient mixing); two independent CMS devices 12, 14 (CMS 1, CMS 2); and two, independent 10-port sample injection valves 15, 16 (V3, V4) each fitted with two, 2 mL sample injection loops 32, 34, 36, 38 (L1, L2, L3, L4). The flow injection system 3 is comprised of a peristaltic pump 60 (PP 1); two, 1 m KOTs 48, 62; a water bath 64 at 95° C. preferably containing five, 10 m KOTs (any device which provides sufficient heating can be used); a cooler 72 at 4° C. containing a 1 m KOT (or any device that provides sufficient cooling); and a fluorescence detector 79 with a 365 nm excitation filter and 450 nm region emission filter (or any detector which provides similar excitation and emission).

A typical analysis using SPS-CMS-FIA will result in four peaks from the FIA gradient, the HAAs in the sample, the THMs in the sample, HAAs in the single-point standard addition and THMs in the single-point standard addition. To obtain those peaks the following series of events occurs:

Sampling

1. The SPS-CMS-FIA 1 will flow either an external calibration standard 21 or drinking water sample 22 containing THMs and HAAs through Valve #1 17 onto CMS #1 12 where the THMs pervaporate across the silicone rubber membrane into a reagent water stream (#3) 26 and the HAAs remain in the original stream 24. The HAAs then load into sample loop #1 32 waiting for injection and the THMs flow to waste 130, both through valve #3 15.
2. At the same time, a syringe pump 146 flows a concentrated standard 144 containing TCAA and chloroform into another stream of drinking water 110 (#5) and into and through valve #2 19, then mixed using the 5 m KOT 23 (preferably 5 m, however 4 m also functions well, or any device which sufficiently mixes the two streams). The flow rates of the syringe pump 146 and reagent water stream 148 are set so the preferable final concentration of TCAA added is ~40 µg/L and chloroform added is ~40 µg/L (though any detectable standard addition is sufficient—as long as the added standard is within the limit of linearity). This standard addition sample 110 flows onto CMS #2 14 where the total THMs pervaporates across the silicone rubber membrane into reagent water stream #4 150. The total HAA standard then flows into sample loop #3 on valve #4 16 while the THM standard flows to waste 152.

Injection

3. The first valve actuation is valve #3 and this injects sample loop #1, containing the HAA sample, into the flow injection analysis system 3. This is done using a reagent water carrier stream 155 (Reagent Water #1) flowing through valve #3 and sample loop #1 and subsequently through valve #4 and into the flow injection system.
4. While sample loop #1 injects into the flow injection system 3, the THM sample loads into sample loop #2 34, waiting for injection of HAAs in sample loop #1 to complete.
5. When sample loop #1 injection completes, valve #3 15 actuates a second time and injects the THM sample in sample loop #2 through valve #4 16 and into the flow injection system 3 using the carrier (reagent water stream line 155).
6. After steps 3-5 are complete, valve #1 17 actuates to flow reagent water #2 through CMS #1 12, this eliminates carry-over associated with the CMS.
7. While steps 3-6 are carried out, the single-point standard addition HAAs load into sample loop #3 39. Once the HAAs and THMs from the drinking water sample are injected completely, valve #4 16 actuates for the first time and the carrier, reagent water stream 155, injects the single-point standard addition HAAs into the flow injection system 3.
8. As sample loop #3 39, the single-point standard addition HAA standard, injects into the flow injection system 3, the single-point standard addition THM standard is loaded into sample loop #4 38, waiting for injection of the single-point HAA standard to complete.
9. When sample loop #3 39 injection is complete, valve #4 16 actuates a second time and injects the single-point standard addition THM standard in sample loop #4 38 into the flow injection system 3 using the carrier (reagent water stream 155).
10. After steps 7-9 are complete, a second 4-port valve (valve #2) 19 actuates to flow reagent water #2 148 through CMS #2 14, this eliminates carry-over associated with the CMS.
11. At this point—all valve actuation is complete. The HAAs from the sample are injected first, followed by the THMs from the sample. Subsequently, the single-point standard addition HAA standard is injected, followed by the single-point standard addition THM standard.

Flow Injection Analysis

12. The HAAs and THMs from the sample and single-point standard addition flow into the same flow injection system for analysis. Both sample and standard use the same reagents, water bath, and detector. The HAA sample analysis is described below; however, keep in mind that the THM sample, HAA standard addition and THM standard addition all experience the same chemical environment.
13. The HAA sample is first mixed with a 1% oxalic acid solution 46 in a 1 m KOT 48 (or any device which sufficiently mixes). The oxalic acid reagent is a free available chlorine (FAC) mask, and has been experimentally optimized to mask up to 10 mg/L FAC solutions, which is about a factor of 2.5 times higher than the MCL for FAC (4 mg/L).
14. A 3.2 M sodium hydroxide reagent 50 then flows into the reaction stream 44 and mixes in a 1 m KOT 62 (or any device that adequately mixes), which neutralizes the oxalic acid and creates a highly basic solution prior to mixing with nicotinamide.
15. 3.0 M nicotinamide 52 then mixes with the highly basic reaction stream 157 and flows through a series of three, 10 m KOTs 64 (for a total of 30 m) at 95° C. (or any device which provides sufficient heating, not limited to the KOTs). At this high temperature, the nicotinamide reacts with THMs and HAAs in basic solution to form a fluorescent product.
16. After heating, the HAA-nicotinamide product is cooled using a 1 m KOT 72 at 4° C. and then flows to the fluorescent detector 79 with 365 nm excitation and 450 nm emission and subsequently out to waste 80.

Thus, ultimately, through such a 16-step process, a remote, on-line drinking water monitoring system of this type provides reliability that every individual, near-real time, on-line monitoring analysis of THMs and HAAs requires. The on-line analysis of Total THMs and Total HAAs with the addition of single point standard addition provides for more reliable, long term results.

As shown in FIG. 1, then, in addition to the calibration component, the overall system 1 basically includes an FIA flow injection analyzer 10 (here a modified FIA Lab 2000) with two capillary membrane sampling devices 12, 14 that initially separates the volatile trihalomethanes into a separate stream of water (purified reagent water) 15 from the drinking water sample stream (that retains the non-volatile haloacetic acids therein). The initial drinking water sample 22 is supplied through a line 11 that is transported by a pump 13 (any type of pump may be utilized, although a peristaltic pump commonly associated with the FIA Lab 2000 system is preferred for this purpose) at any desired rate, although preferably, for suitable test purposes, the water sample flows at a rate of 1.0 mL/minute through the pump 13 and the reagent water stream at 0.1 mL/min. The sampling component 12 then transports the two different streams of halogenated byproducts 24, 26 to an electrostatically actuated ten-port sample injection valve 15 fitted with two water injection sample loops (L1, L2) 32, 34. This valve 54 is fully automated using a software package (such as Peak Simple from SRI Instruments Inc.) and a single channel serial port data acquisition system (not illustrated) (this acquisition system also collects the data from fluorescence detectors, such as Model 420 from Waters Inc.)(any suitable automating software and data acquisition systems and fluorescence detectors may be utilized for these purposes). The valve 15 permits alternating injection of either stream into a stream of reagent water carrier 26 for delivery into a mixing manifold. Within the mixing manifold 44 is then introduced a stream of oxalic acid 46 (preferably, though not necessarily 1.0% aqueous solution thereof; and alternative chlorine masking agents could be used) to aid in reducing unwanted interferents (such as hypochlorous acid, hypochlorite ion, etc.) within the two test streams within a reactor coil 48 (of any type, although preferably such a coil is made from polymeric material and has an outer diameter of about 1.6 mm, an inner diameter of 0.75 mm, and a length of about 5 meters). After mixing the oxalic acid into the stream, the resultant solution is then further reacted with sodium hydroxide 50 (preferably, though not necessarily, a 3.2 M aqueous solution thereof) and a nicotinamide solution 52 (preferably, though not necessarily, a 3.0 M aqueous solution thereof). All three reactants may be delivered for mixing with the test streams through separate pumps, one pump for all three, or even the same pump as the water samples themselves. In this schematic, one pump 60 is utilized for all three reactants. Any flow rate may be set for the introduction of such reactants, although it is preferable that the reagent water is set at a flow rate of about 0.7 mL/minute, and the oxalic acid, sodium hydroxide and nicotinamide reagents are set at a flow rate of about 0.1 mL/minute each. These three-reactant plus water stream mixture is combined within a second reactor coil 62 (that is preferably fitted with a heating knitted open tubular coil of outer diameter 1.6 mm, inner diameter 0.75 mm, and a length of 30 M though the length and type of reactor coil can vary) that is heated to a preferable temperature of about 97° C. (in actuality, any temperature will be suitable for this device, although the higher the temperature the faster the result) within a further reactor bath 64. The transport rate remained static and the resultant fluorescing solution was then cooled to reduce any bubbles that might form within the resultant stream (preferably, an ice bath is utilized) within the third reactor coil 72 and to maximize fluorescent intensity therein. From there, the resultant solution was introduced within the fluorescent detector 78. Such a detector 78 then analyzes the different fluorescing THM4 or HAA9 compounds in the drinking water samples or standard addition samples depending upon which stream is currently allowed delivery via the ten-port valves 15. With standard addition signals measured, determinations of THM4 and HAA9 compound quantities within the initial drinking water sample are then made. The samples are then ejected out of the detector 78 into a waste receptacle 80.

Method Detection Limit, Accuracy and Precision of the SPS-CMS-FIA

The SPS-CMS-FIA was calibrated using external calibration and the inventive single-point-standard calibration and standard addition calibration. For HAA9 species, the external calibration range is from 22.5 to 100 µg/L with a check standard concentration of 31.5 µg/L (FIG. 8). The single-point standard was 41.2 µg/L TCAA and analyzed on every run. For THM4 species, the external calibration range is from 24 to 98 µg/L with a check standard concentration of 30.0 mg/L. The single-point standard was 41.2 µg/L chloroform and analyzed on every run.

A modified USEPA protocol is used to determine the method detection limit (MDL), mean % recovery, and % relative standard deviation for Total THMs and Total HAAs. The MDL for Total THMs and Total HAAs was determined by analyzing seven consecutive check standards containing TCAA and chloroform and determining the concentrations of each using standard addition. The standard deviation of the check standard concentrations was determined and multiplied by Student's t-value for 6 degrees of freedom (t-value=3.143). The mean % recovery, an estimate of accuracy, was determined by calculating the concentration of Total THMs or Total HAAs in each check standard, dividing by the prepared concentration and multiplying by 100%. The % RSD, an estimate of precision, was determined by dividing the standard deviation of Total THM or Total HAA concentration by the average calculated concentration and multiplying by 100%.

Using this standard addition protocol, the MDL for Total THMs was 6.1 µg/L. The mean % recovery was 104% and the % RSD was 8%. The MDL for Total HAAs was 8.4 µg/L with a mean % recovery of 107% and % RSD of 11%.

The MDL, accuracy and precision results for external calibration are presented in Table 1. The MDL, accuracy and precision values for external calibration and single-point standardization compare well. The MDL is within a factor of 2 and shows acceptable mean % recovery and % RSD data.

TABLE 1

External Calibration MDL, Accuracy and Precision Results

| Species | Check Std. Conc. (µg/L) | MDL (µg/L) | Mean % Recovery | % RSD |
|---|---|---|---|---|
| HAA9 | 31.5 | 1.2 | 88.9 | 1.3 |
| THM4 | 30.0 | 1.0 | 97.7 | 1.0 | on-Line Monitoring Using the CMS-FIA Standard Addition Instrument

To evaluate the CMS-FIA Standard Addition instrument, an on-line monitoring study was conducted in central Arkansas. The CMS-FIA-SA instrument used standard addition to simultaneously calibrate and analyze samples every 90 minutes for both Total THMs and Total HAAs. The instrument was run continuously for 10.5 hours analyzing 7 samples directly from the distribution system. To evaluate the instrument, the bias was calculated for each run by comparing the CMS-FIA-SA results for Total THMs or Total HAAs directly to the respective USEPA method for THMs or HAAs. The bias is calculated as "experimental value–true value," for individual measurements where the experimental value is the concentration for Total THMs or Total HAAs reported by the CMS-FIA-SA and the true value is the USEPA method for THMs or HAAs. The average bias and standard deviation is then calculated for Total THMs or Total HAAs.

Over seven individual measurements for both THMs and HAAs, the average bias for Total THMs was −12±6 µg/L and the average bias for Total HAAs was 20±12 µg/L.

Another important analytical value to consider is analyte tracking which is evaluated using an instantaneous concentration change between the CMS-FIA-SA and USEPA methods for THMs or HAAs. Analyte tracking is determined by subtracting the concentration at time #2 from the concentration at time #1, where time #2 is later than time #1 and in consecutive order, for both CMS-FIA-SA and the USEPA method. Using this approach, there is a 33% random chance where both methods will agree. For Total THMs, the CMS-FIA-SA had a 50% tracking agreement compared to USEPA 524.2 and for Total HAAs, the CMS-FIA-SA had 66% tracking agreement compared to USEPA 552.3.

Thus, combined with the on-line water monitoring system described above, the inventive calibration component provides highly effective and reliable standardization for improved measurements in terms of overall reliability. Hence, the overall system is the most reliable remote system of its kind for water purity analysis.

The preceding examples are set forth to illustrate the principles of the invention, and specific embodiments of operation of the invention. The examples are not intended to limit the scope of the method. Additional embodiments and advantages within the scope of the claimed invention will be apparent to one of ordinary skill in the art.

What we claim is:

1. A method of analyzing drinking water samples in an on-line procedure and at a remote location along a drinking water supply line, said method comprising:
   a) providing at least one initial stream of drinking water that has been disinfected with chlorinated or chloraminated disinfectants within a first tube;
   b) separating said initial drinking water stream of step "a" into at least two different subsequent streams, wherein i) a first separated stream of drinking water is transferred directly into a second tube, and ii) a second separated stream of drinking water is transferred into a third tube wherein it is injected remotely with a standard calibration water sample, wherein said standard calibration water sample includes a predetermined concentration of trihalomethanes and haloacetic acids therein;
   c) providing a first separate stream of reagent water, wherein said first reagent stream is present within a fourth tube into which said second tube including said first separated stream of drinking water is introduced to form a first capillary membrane sampling device;
   d) providing a second separate stream of reagent water, wherein said second reagent stream is present within a fifth tube into which said third tube including said second separated stream of drinking water and said standard calibration water sample is introduced to form a second capillary membrane sampling device;
   e) transporting said first separated stream of drinking water through said first capillary membrane sampling device, such that the majority of all volatile trihalomethanes present within said first separated drinking water stream traverse a membrane of said first capillary membrane sampling device from of said second tube into said first stream of reagent water within said fourth tube to form a first trihalomethane-containing stream, and wherein any haloacetic acids present within said first separated drinking water stream will remain therein and within said second tube to form a first haloacetic acid-containing stream;
   f) transporting said second separated stream of drinking water through said second capillary membrane sampling device, such that the majority of all volatile trihalomethanes present within said second separated drinking water stream traverse a membrane of said second capillary membrane sampling device from said third tube into said second stream of reagent water within said fifth tube to form a second trihalomethane-containing stream, and wherein any haloacetic acids present within said second separated drinking water stream will remain therein and within said third tube to form a second haloacetic acid-containing stream;
   g) transporting the first trihalomethane-containing stream and the first haloacetic acid-containing stream to a first multi-port injection valve, wherein said first multi-port valve is configured to inject either said first trihalomethane-containing stream or said first haloacetic acid-containing stream to a first mixing manifold one at a time, while the other of said first trihalomethane or haloacetic acid containing streams is passed through a return line until said first multi-port injection valve is activated to send the other of said first trihalomethane or haloacetic acid containing streams to said first mixing manifold;
   h) mixing either of said first trihalomethane or haloacetic acid containing streams from step "g" with a base and a fluorescing compound when sent to and present within said first mixing manifold to form a first fluorescing trihalomethane-containing stream or a first fluorescing haloacetic acid-containing stream therein;
   i) transporting either of said first fluorescing trihalomethane-containing stream or said first fluorescing haloacetic acid-containing stream of step "h" to a fluorescence detector to determine a concentration of either total trihalomethanes or total haloacetic acids within each of said first fluorescing streams through fluorescence detection; wherein only one of said first fluorescing trihalomethane-containing or said first fluorescing haloacetic acid-containing streams will be analyzed at any one time, while the other of said first fluorescing trihalomethane or haloacetic acid containing streams is passed through a return or waste line;
   j) simultaneously transporting the second trihalomethane-containing stream and the second haloacetic acid-containing stream to a second multi-port injection valve, wherein said second multi-port valve is configured to inject either said second trihalomethane-containing stream or said second haloacetic acid-containing stream to a second mixing manifold one at a time, while the other of said second trihalomethane or haloacetic acid containing streams is passed through a return line until said second multi-port injection valve is activated to send the other of said second trihalomethane or haloacetic acid containing streams to said second mixing manifold;
   k) mixing either of said second trihalomethane or haloacetic acid containing streams from step "j" with a base and a fluorescing compound when sent to and present within said second mixing manifold to form either a second fluorescing trihalomethane-containing stream or a second fluorescing haloacetic acid-containing stream therein;
   l) transporting either of said second fluorescing trihalomethane-containing stream or said second fluorescing haloacetic acid-containing stream of step "k" to a fluorescence detector to determine a concentration of either total trihalomethanes or total haloacetic acids within each of said second fluorescing streams through fluorescence detection; wherein only one of said second fluorescing trihalomethane-containing or said second fluorescing haloacetic acid-containing streams will be analyzed at any one time, while the other of said second fluorescing trihalomethane or haloacetic acid containing streams is passed through a return or waste line;
   and m) calculating total haloacetic acid and trihalomethane compound concentrations of all of said first and second fluorescing trihalomethane-containing and haloacetic acid-containing streams based on fluorescence levels thereof in relation to a calibration point based upon the standard calibration water sample containing predetermined concentrations of trihalomethanes and haloacetic acids introduced within said third tube;

wherein steps a) through l) are then repeated in intervals of between 10 and 120 minutes.

* * * * *